United States Patent [19]

Oishi et al.

[11] Patent Number: 4,728,189

[45] Date of Patent: Mar. 1, 1988

[54] ATOMIC ABSORPTION SPECTROPHOTOMETER

[75] Inventors: Konosuke Oishi, Mito; Koichi Uchino, Katsuta; Hideo Yamada, Katsuta; Seigo Kamitake, Katsuta; Masao Hashimoto, Katsuta, all of Japan

[73] Assignee: Hitachi, Ltd. Hitachi Instrument Eng., Japan

[21] Appl. No.: 6,170

[22] Filed: Jan. 23, 1987

[30] Foreign Application Priority Data

Jan. 24, 1986 [JP] Japan .................................. 61-12012

[51] Int. Cl.$^4$ .......................... G01J 3/42; G01N 21/74
[52] U.S. Cl. ..................................... 356/312; 356/326; 356/307
[58] Field of Search ............... 356/307, 312, 315, 316, 356/326, 328; 364/498

[56] References Cited

U.S. PATENT DOCUMENTS 4,377,342  3/1983  Koizumi et al. .................... 356/312
4,449,820  5/1984  Koizumi et al. .................... 356/315

Primary Examiner—F. L. Evans
Attorney, Agent, or Firm—Antonelli, Terry & Wands

[57] ABSTRACT

An absorption profile indicative of a relation in atomic absorption spectroscopy between the absorbance of a desired element and time has a constant half-width independent of the concentration of the desired element in a sample, and hence the half-width of absorption profile with respect to the desired element can be previously determined from data which is obtained by the measurement of a standard sample. In an atomic absorption spectrophotometer herein disclosed, the half-width of absorption profile is previously determined in the above-mentioned manner, and the true peak value of an absorption profile obtained by measuring a sample which contains the desired element at a high concentration, is calculated using the time width of this absorption profile at a predetermined absorbance and the previously-determined half-width.

9 Claims, 6 Drawing Figures

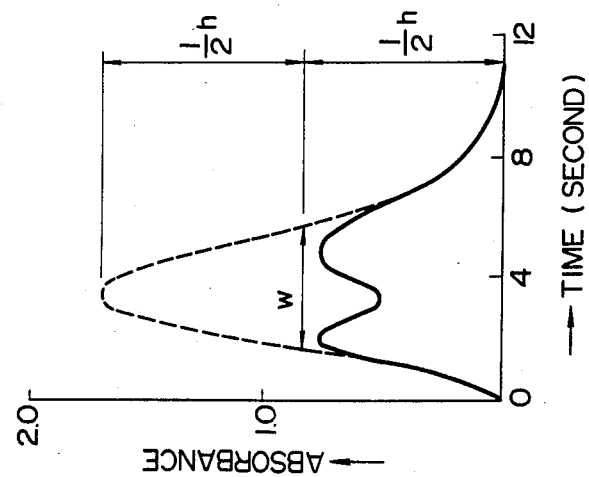
FIG. IA
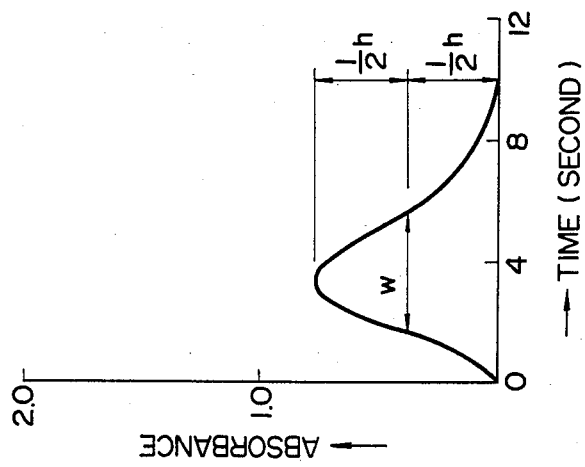
FIG. IB
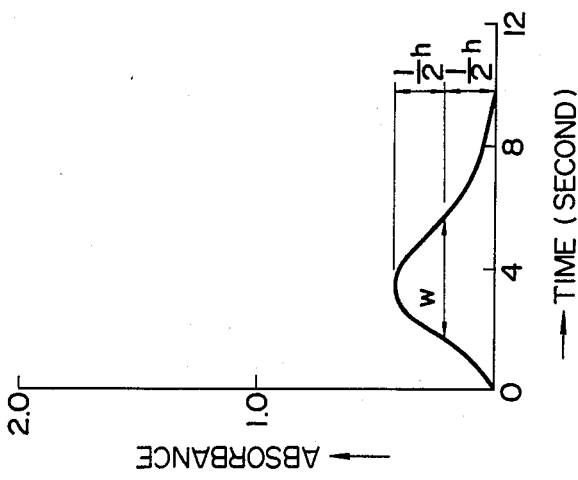
FIG. IC

ATOMIC ABSORPTION SPECTROPHOTOMETER

BACKGROUND OF THE INVENTION

The present invention relates to atomic absorption spectrophotometers, and more particularly to an atomic absorption spectrophotometer suitable for quantitatively determining a very small amount of metallic element dissolved in an aqueous solution.

In an atomic absorption spectrophotometer, as described in U.S. Pat. No. 4,377,342, a desired element contained in a liquid sample is converted by an atomizer such as a graphite tube into atomic vapor, and the atomic vapor is irradiated with light from a light source, to quantitatively determine the desired element on the basis of the degree of absorption of light by the atomic vapor. In such a case, the density of atomic vapor within the graphite tube increases as the concentration of the desired element in the sample is larger, but the absorption of light by the atomic vapor saturates at an absorbance of about 2.0, though this value varies slightly, depending upon the kind of the desired element. Thus, it is impossible to quantitatively determine the desired element which is contained in the sample at concentrations greater than a value.

In order to make it possible to quantitatively determine a desired element which is contained in a liquid sample at high concentrations and causes the above saturation phenomenon, an analytical method is proposed in the above-referred U.S. Pat. No. 4,377,342. In this method, attention is paid to the absorbance vs. time curve (that is, absorption profile) of the desired element, and the element is quantitatively determined on the basis of the time width of the absorption profile at a predetermined absorbance. That is, the analytical method using a time width of absorption profile is based upon a fact that the time width of absorption profile at the predetermined absorbance increases with increasing concentration of the desired element. In this method, however, the gradient of tangent to a working curve decreases greatly with increasing concentration of the desired element, as shown in FIGS. 6 and 7 of the above-referred U.S. Patent, and hence it is not always possible to determine the desired element accurately.

SUMMARY OF THE INVENTION

It is an object of the present invention to provide an atomic absorption spectrophotometer capable of determining a desired element which is contained in a liquid sample at a high concentration, very accurately.

The present inventors studied those absorbance vs. time curves (namely, absorption profiles) of a desired element which were obtained by measuring a plurality of samples containing the desired element at different concentrations, and found the following facts.

(i) The absorption profiles have the same half-width.

(ii) The peak value h of an absorption profile, the half-width w thereof, and the time width v of the absorption profile at an absorbance k are related to each other by the following equation:

$$\frac{w}{v} = \frac{\frac{1}{2}h}{h-k}$$

The above facts make it possible to quantitatively determine a desired element even when the absorption profile of the desired element which is contained in a sample at a high concentration, has a plurality of peaks and thus it is impossible to find a true peak of absorbance directly from the absorption profile. That is, the half-width w is previously determined from an absorption profile which is obtained by the measurement of a sample containing the desired element at a low concentration and has only a single peak, and a true peak value h is calculated from the above equation.

In more detail, according to the present invention, even when a top portion of the absorption profile of a desired element which is contained in a liquid sample at a high concentration, lies within a saturation region of absorbance, the true peak of the absorption profile can be determined by utilizing the fact that the half-width of absorption profile is constant, independently of the concentration of the desired element. That is, the half-width w is previously determined from an absorption profile which is obtained by measuring a standard sample which contains the desired element at a low concentration, and the time width v of the absorption profile of the desired element contained in a sample which is to be analyzed, at a predetermined absorbance k is measured, to determine the true peak value h of the latter absorption profile from the above factors w, k and v.

BRIEF DESCRIPTION OF THE DRAWINGS

FIGS. 1A, 1B and 1C are graphs showing absorption profiles of an element corresponding to concentrations $C_1$, $C_2$ and $C_3$ thereof in a liquid sample.

DESCRIPTION OF THE PREFERRED EMBODIMENT

The principle of the present invention will first be explained, with reference to FIGS. 1A, 1B, 1C and 2.

FIGS. 1A to 1C are graphs showing absorption profiles of an element corresponding to concentrations $C_1$, $C_2$ and $C_3$ thereof in a sample, and FIG. 1C shows a case where the absorption profile rolls over because of the high concentration $C_3$ of the element. When the absorption profile of FIG. 1C is corrected by a nonlinear least squares method on the basis of measured values corresponding to values of absorbance less than one-third of a true peak value of the above absorption profile, a corrected profile is obtained as indicated by a broken curve in FIG. 1C. In the non-linear least squares method, it is assumed that the absorption profile is expressed by the following function f:

$$f = at^b \exp(-ct) \ldots \quad (1)$$

where a, b and c are coefficients which are to be determined by measurement.

As explained in the foregoing, absorption profiles of an element corresponding to different concentrations thereof have the same half-width.

Further, as a result of the detailed study of the above absorption profiles, it was found that the coefficient a of the equation (1) was proportional to the concentration of the element, but the coefficients b and c were constant independently of the concentration of the element. By utilizing the above fact, the true peak of an absorption profile having rolled over can be determined without correcting the absorption profile by the non-linear least squares method. Now, a novel method of determining the true peak of an absorption profile will be explained, with reference to FIG. 2.

Figure 2:
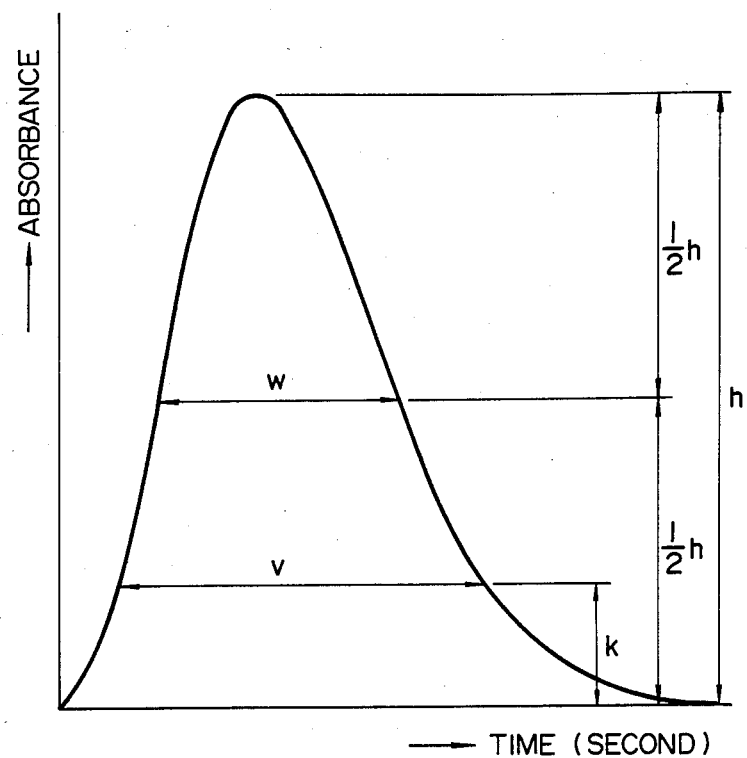
FIG. 2 is a graph for explaining a method of calculating the true peak of an absorption profile.

FIG. 2 is a graph for explaining a method of calculating a peak value of absorption profile. Referring to FIG. 2, the peak value h of an absorption profile, the half-width w thereof, and the time width v of the absorption profile at a given absorbance k are related to each other by the following equation:

$$\frac{w}{v} = \frac{\frac{1}{2}h}{h - k} \qquad (2)$$

Accordingly, the peak value h is given by the following equation:

$$h = \frac{2wk}{2w - v} \qquad (3)$$

As mentioned previously, the half-width w of absorption profile with respect to a desired element is constant independently of the concentration of the desired element. Hence, the true peak value of an absorption profile can be determined only by measuring the time width of the absorption profile at an appropriate absorbance, provided that the half-width w is previously determined from an absorption profile which is obtained by the measurement of a sample containing the desired element at a low concentration, and which does not roll over.

Figure 3:
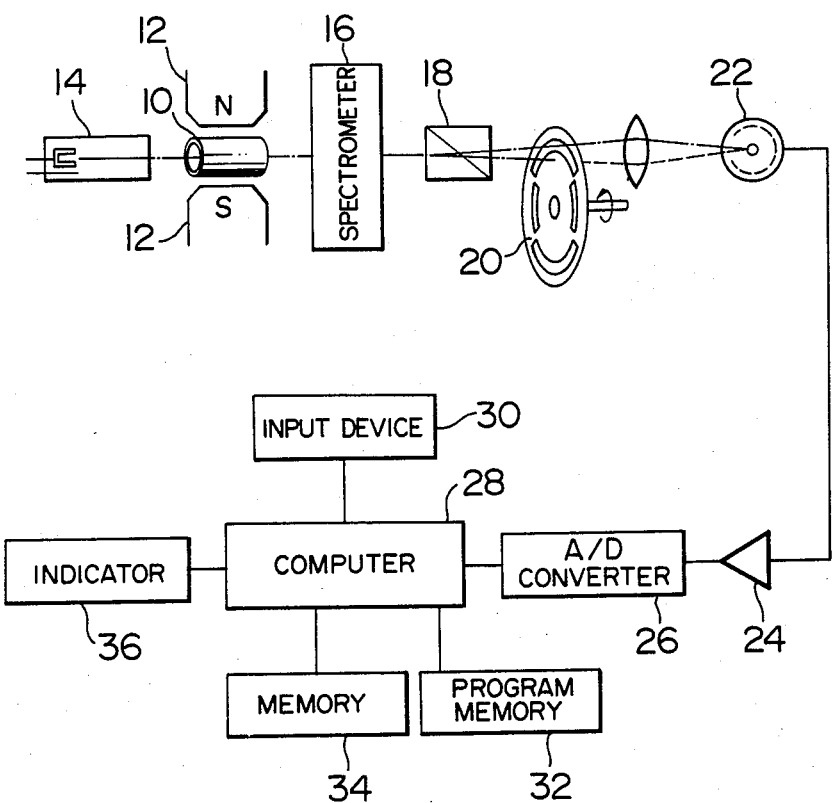
FIG. 3 is a block diagram showing an embodiment of an atomic absorption spectrophotometer according to the present invention.

Now, explanation will be made of an embodiment of an atomic absorption spectrophotometer according to the present invention. FIG. 3 is a block diagram showing the above embodiment. Referring to FIG. 3, a magnetic field generated by a permanent magnet 12 is applied to a graphite tube 10, into which a liquid sample containing a desired element is introduced. Electric power is supplied to a graphite furnace containing the graphite tube 10, to heat the desired element to atomic vapor. A light beam from a light source 14 passes through the atomic vapor, and then enters a spectrometer 16, to take out only a wavelength component corresponding to a predetermined analytical line. The light beam from the spectrometer 16 is separated by a fixed polarizer 18 into a light component $P_{11}$ having the plane of vibration parallel to the magnetic field applied to the graphite tube 10 and another light component $P_{12}$ having the plane of vibration perpendicular to the above magnetic field. The light components $P_{11}$ and $P_{12}$ are alternately received by a detector 22 with the aid of a beam selector 20. It is to be noted that the light component $P_{11}$ has been subjected to the absorption due to the above atomic vapor and the absorption due to background, but the light component $P_{12}$ has been subjected to only the absorption due to background. By detecting the difference in light quantity between the components $P_{11}$ and $P_{12}$, the absorption of light by the atomic vapor can be measured without being affected by the absorption due to background.

Light incident upon the detector 22 is converted into an electric signal whose amplitude corresponds to the intensity of incident light. The electric signal from the detector 22 is amplified by a pre-amplifier 24, and is then converted by an analog-to-digital converter 26 into a digital signal, which is applied to a computer 28. An input device 30 stores a value k of absorbance, at which the time width v of absorption profile is to be measured. A series of standard samples is prepared so that the standard samples contain a desired element at different concentrations, and at least one of absorption profiles of the desired element corresponding to the standard samples does not roll over. The above standard samples are successively measured, and the absorption profile which does not roll over, is used to determine the half-width w. That is, the computer 28 calculates the half-width w from data with respect to the above absorption profile in accordance with a calculation program which corresponds to the equation (2) and is stored in a program memory 32. The half-width w thus determined is stored in a memory 34, together with that relation between the concentration of the desired element and the peak value of absorption profile which is obtained by the measurement of the standard samples. Then, an unknown sample containing the desired element is measured, to obtain the absorption profile of the desired element. The time width v of this absorption profile at the absorbance value k stored in the input device 30 is measured. Then, the true peak value h of the absorption profile is calculated from the above factors w, k and v in accordance with another calculation program which corresponds to the equation (3) and is stored in the program memory 32; and then the concentration of the desired element is determined from the true peak value thus obtained and the concentration-peak relation stored in the memory 34. The concentration thus determined is indicated by an indicator 36.

Figure 4:
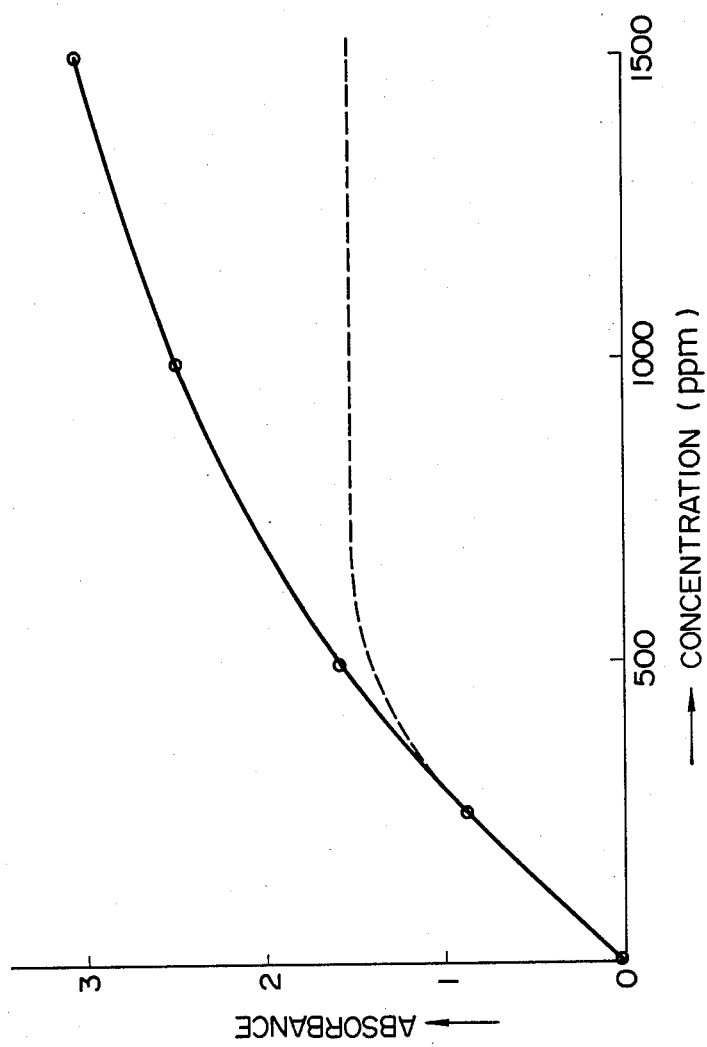
FIG. 4 is a graph showing relations between the concentration of chromium and the absorbance due to chromium vapor which are obtained by the present invention and a prior art.

FIG. 4 is a graph showing relations between chromium concentration and absorbance, for a case where chromium contained in a liquid sample is determined by atomic absorption spectroscopy. In FIG. 4, a solid curve indicates the above relation obtained by the present invention, and a broken curve indicates that obtained by a prior art. As is apparent from FIG. 4, according to the present invention, the measurable concentration range is two or more times wider than that of the prior art.

As has been explained in the foregoing, according to the present invention, a maximum measurable concentration of a desired element in atomic absorption spectroscopy can be made higher, as compared with that of the prior art.

We claim:

1. An atomic absorption spectrophotometer including atomizer means for heating a sample which is to be analyzed, to atomic vapor, a light source for irradiating the atomic vapor with light, and a detector for detecting light having passed through the atomic vapor, for forming an absorption profile indicative of a relation between the absorbance due to atomic vapor of a desired element contained in the sample and time, on the basis of a signal from the detector, to determine the concentration of the desired element from the peak value of the absorption profile, said atomic absorption spectrophotometer comprising means for previously determining the half-width w of absorption profile from data which is obtained by measuring a standard sample, and for determining the true peak value h of the absorption profile of the desired element contained in the to-be-analyzed sample, on the basis of the time width v of said absorption profile at a predetermined absorbance k and the previously-determined half-width w.

2. An atomic absorption spectrophotometer according to claim 1, wherein said standard sample contains the desired element at a low concentration.

3. An atomic absorption spectrophotometer according to claim 1, wherein said true peak value h is calculated from the following equation:

$$h = \frac{2wk}{2w - v}$$

4. An atomic absorption spectrophotometer according to claim 1, wherein said atomizer means is applied with a magnetic field.

5. An atomic absorption spectrophotometer according to claim 4, wherein said magnetic field is generated by a permanent magnet.

6. An atomic absorption spectrophotometer according to claim 1, wherein a polarizer is interposed between said atomizer means and said detector.

7. An atomic absorption spectrophotometer according to claim 6, wherein said polarizer is a fixed polarizer.

8. An atomic absorption spectrophotometer according to claim 6, wherein a beam selector is interposed between said polarizer and said detector.

9. An atomic absorption spectrophotometer according to claim 1, wherein said atomizer means is a graphite tube.

* * * * *